United States Patent
Tettamanti et al.

(10) Patent No.: US 12,042,665 B2
(45) Date of Patent: Jul. 23, 2024

(54) USING LASER LIGHT FOR TREATING MELASMA AND RELATED HYPERPIGMENTATION DISORDERS

(71) Applicant: Fotona d.o.o., Ljubljana (SI)

(72) Inventors: Marcelo Tettamanti, Stuart, FL (US); Julio Cezar Velez Ocampo, Bogota (CO); Sebastian Velez Ocampo, Bogota (CO); Dejan Skrabelj, Lesce (SI); Irena Hreljac, Ljubljana (SI)

(73) Assignee: Fotona d.o.o., Ljubljana (SI)

( * ) Notice: Subject to any disclaimer, the term of this patent is extended or adjusted under 35 U.S.C. 154(b) by 1109 days.

(21) Appl. No.: 16/574,759

(22) Filed: Sep. 18, 2019

(65) Prior Publication Data

US 2021/0077824 A1    Mar. 18, 2021

(51) Int. Cl.
| | |
|---|---|
| *A61N 5/06* | (2006.01) |
| *A61B 18/00* | (2006.01) |
| *A61B 18/20* | (2006.01) |
| *A61N 5/067* | (2006.01) |

(52) U.S. Cl.
CPC .......... *A61N 5/0616* (2013.01); *A61B 18/203* (2013.01); *A61N 5/062* (2013.01); *A61N 2005/0626* (2013.01); *A61N 5/067* (2021.08)

(58) Field of Classification Search
CPC .......... A61B 18/203; A61B 2018/0047; A61B 2018/00577; A61N 2005/0626; A61N 5/0616; A61N 5/062; A61N 5/067
USPC ..................................... 606/2–19; 607/88–94
See application file for complete search history.

(56) References Cited

U.S. PATENT DOCUMENTS

| | | | |
|---|---|---|---|
| 2004/0073277 A1* | 4/2004 | Geronemus | A61K 41/0076 607/88 |
| 2005/0049582 A1* | 3/2005 | DeBenedictis | A61B 18/20 606/9 |
| 2005/0065503 A1* | 3/2005 | Anderson | A61B 18/203 606/9 |

(Continued)

OTHER PUBLICATIONS

Drs. Sebastián and Julio Cesar Velez Ocampo, *New Protocol for Long-Term Results in Melasma Treatments with Nd: YAG Laser Multi-pulse Skin Conditioning Approach*, Clinical Bulletin, Feb. 28, 2019, J. Laha, vol. 2019, No. 1; p. CB04, Published by the Laser and Health Academy.

*Primary Examiner* — Jonathan T Kuo
*Assistant Examiner* — Vynn V Huh
(74) *Attorney, Agent, or Firm* — Renner, Otto, Boisselle & Sklar, LLP

(57) ABSTRACT

Methods and apparatus for treating melasma and/or related hyperpigmentation disorders of a patient are disclosed. The treatment includes delivering laser pulses onto a body of the patient, wherein the delivering laser pulses includes two or more of the following steps: 1) delivering laser pulses $p_1$ onto the body, wherein each pulse of the laser pulses $p_1$ is configured to have a diameter of at least 100 μm and a duration of at most 1 μs; 2) delivering laser pulses $p_2$ onto the body, wherein each pulse of the laser pulses $p_2$ is configured to have a diameter of at least 100 μm and a duration of more than 1 μs; 3) delivering laser pulses $p_3$ onto the body, wherein each pulse of the laser pulses $p_3$ is configured to comprise a plurality of microbeams, each microbeam having a diameter below 1 mm.

20 Claims, 4 Drawing Sheets

(56) References Cited

U.S. PATENT DOCUMENTS

Figure 1:
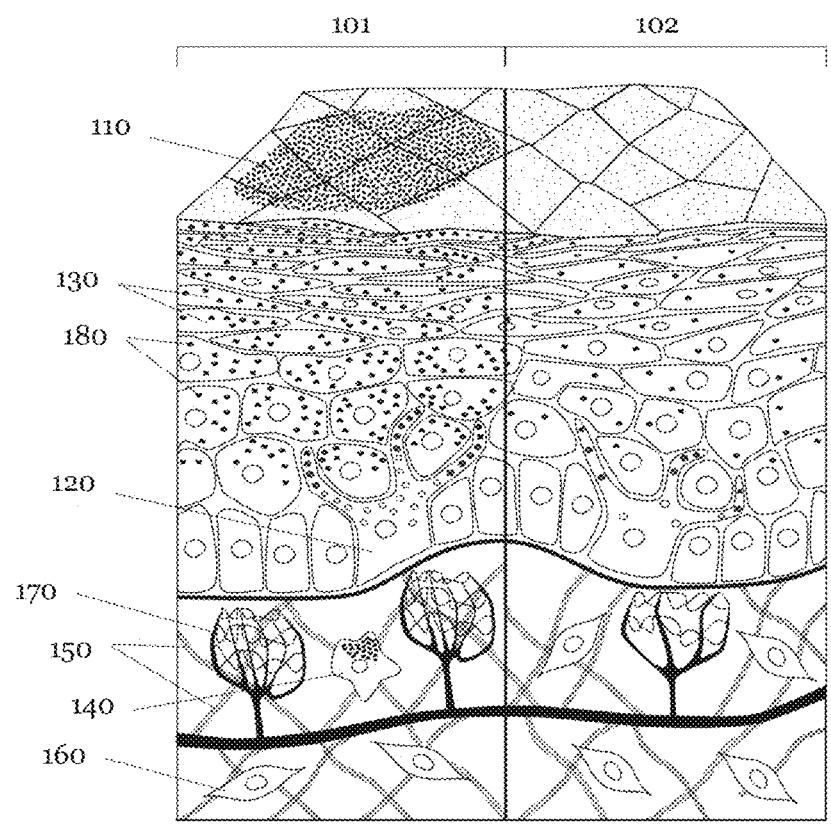

| | | | |
|---|---|---|---|
| 2007/0038206 A1* | 2/2007 | Altshuler | A46B 15/0036 |
| | | | 606/20 |
| 2007/0198068 A1* | 8/2007 | Chan | A61B 18/203 |
| | | | 607/88 |
| 2008/0208179 A1* | 8/2008 | Chan | A61B 18/203 |
| | | | 514/474 |
| 2018/0071024 A1* | 3/2018 | Harris | A61Q 19/00 |

* cited by examiner

USING LASER LIGHT FOR TREATING MELASMA AND RELATED HYPERPIGMENTATION DISORDERS

1. TECHNICAL FIELD

The present invention relates to treatment of melasma and/or related hyperpigmentation disorders using (a combination of) different delivery modes of laser light.

2. BACKGROUND OF THE INVENTION

Melasma is a common hyperpigmentation disorder that typically occurs as symmetric hyperpigmented patches with irregular borders on the nose, forehead, chin, malar cheeks, mandible and rarely upper chest and extremities. The prevalence rate of melasma in the general population was estimated to be around 1% but can be up to 50% in high-risk populations—women and people with darker skin types.

Melasma is a complex condition. Its pathogenesis usually involves more than one of the following: hyperactivity of melanocytes; increase in melanocyte numbers in affected areas; presence of dermal melanophages; vascular dilation and proliferation and chronic mild perivascular inflammation. Major factors contributing to the development of melasma are exposure to UV light, hormonal influences, oxidative stress and family history, indicating a genetic predisposition component. Histologically, hyperpigmentation in melasma can be epidermal, dermal or a mixture of both. In the epidermal variation, there are increased numbers of melanosomes in the epidermal keratinocytes and melanocytes. In the dermal variation, the hyperpigmentation is mostly located in melanophages and is often accompanied by accumulation of elastin and an increase in the number of blood vessels.

There are multiple proposed mechanisms responsible for melasma formation. According to one of the proposed mechanisms, exposure to UV light can induce the formation of reactive oxygen species (ROS), and patients with melasma have been found to have higher markers of oxidative stress. ROS can trigger melanogenesis by various cellular signalling pathways. One of the major pathways of UV light induced melasma is the secretion of SCF (stem-cell factor) by melanocytes which activates the downstream c-kit protein kinase pathway that induces melanogenesis. Vascular endothelial growth factor (VEGF) overexpression has also been implicated in melasma which is evident in hyperproliferation of blood vessels that is a common component of the condition. Hormones also play an important role in melasma development—the risk of developing melasma in women is significantly higher, with even higher occurrence in pregnancy. The most probable mechanism of hormone-related implication is the cross-activation of melanogenesis by hormone-inducer secondary messenger cAMP (cyclic AMP; AMP: adenosine monophosphate).

Various approaches are known for treating melasma and related hyperpigmentation disorders. However, these have limited success rates. Most of the gold standard treatments use either topical or systemic pharmacologically active substances.

Some treatments focus on limiting the onset of hyperpigmentation by minimizing conditions that can lead to oxidative stress. Topical UV shields are commonly recommended to affected individuals as a preventative measure. Other topical treatments include antioxidants which reduce the oxidative stress-mediated signalling. Antioxidants are also frequently given systemically as an adjuvant treatment.

Another branch of treatments focuses on the prevention of melanin synthesis. The standard of this branch of treatment for melasma is topical or oral hydroquinone, a small molecule that inhibits tyrosinase, a key enzyme in melanin synthesis. Although administering hydroquinone has shown effectiveness in reducing melasma, prolonged treatment with hydroquinone has been linked to depigmentation and ochronosis, a pigment accumulation disorder that is very difficult to treat. Because of this, some countries have banned the use of hydroquinone in the treatment of hyperpigmentation disorders. Besides hydroquinone, topical treatment with retinoids, substances with bleaching effect, is also common. As localized inflammation is a component of melasma, topical corticosteroids are sometimes applied to the affected regions to reduce inflammation. However, corticosteroids can usually be prescribed for limited time periods only, because there are various side-effects connected to their prolonged administration.

Because of the complex pathogenesis of melasma, a combined topical therapy is usually used to fight different underlying causes and symptoms. Kligman's formula is an exemplary combined topical therapy containing hydroquinone, retinoic acid and corticosteroids. Though effective, prolonged application can be problematic due to the side effects connected to all three components. Moreover, such therapies typically rely on regular patient compliance which generally reduces over time, leading to recurrence of symptoms.

Besides topical and oral pharmacological treatments, therapies using mechanical or electromagnetic energy have been shown effective in treating melasma. They can work by destroying the accumulated pigments and by inducing tissue turnover. The advantage of such treatments is the absence of chemical agents that interfere with melanin synthesis. This is beneficial, as melanin is involved in many systemic processes in the body, such that the inhibition of melanogenesis comes with undesired effects, even when used only locally.

Also lasers have been used to selectively destroy over-accumulated melanin in melanosomes. For this purpose, lasers are typically used that emit wavelengths absorbed by melanin. Moreover, the lasers must be able to produce extremely short pulses (picosecond to nanosecond range) with high powers. These pulses may then cause destruction of melanin-containing organelles without damaging other skin components.

However, the known approaches to treat melasma and/or related hyperpigmentation disorders are less than optimal. Hence, there is a need for improved treatment of melasma and/or related hyperpigmentation disorders.

3. SUMMARY

This Summary is provided to introduce in a simplified form a selection of concepts that are further described below in the Detailed Description. This Summary is not intended to identify key features or essential features of the claimed subject matter, nor is it intended to limit the scope of the claimed subject matter.

According to an aspect, a method for treating melasma and/or related hyperpigmentation disorders of a patient is provided. The method comprises delivering laser pulses onto a body of the patient. The delivering of the laser pulses includes two or more of the following steps: According to a first step, laser pulses $p_1$ are delivered onto the body, wherein each pulse of the laser pulses $p_1$ is configured to have a diameter of at least 100 μm and a duration of at most 1 μs.

According to a second step, laser pulses $p_2$ are delivered onto the body, wherein each pulse of the laser pulses $p_2$ is configured to have a diameter of at least 100 μm and a duration of more than 1 μs. According to a third step, laser pulses $p_3$ are delivered onto the body, wherein each pulse of the laser pulses $p_3$ is configured to comprise a plurality of microbeams, each microbeam having a diameter below 1 mm.

Thus, a method is provided in which different laser light parameters are delivered onto the body (e.g. onto a treatment area on the body) in sequential steps which targets different processes underlying the melasma condition. Hence, a more holistic treatment may be enabled. Such a combined treatment using laser light (e.g. from a single apparatus, done by a single operator, possibly in a single treatment session) may be used to tackle different aspects of the (pathogenesis of) melasma and related hyperpigmentation disorders, e.g. melanin destruction, tissue renewal, reduction in hyperproliferated blood vessels and reduction of local inflammation. As a result, a new level of efficiency and precision of treatment may be provided. Better therapy results may be achieved in a shorter amount of time, which may contribute to minimising the variations that arise from reduced patient compliance over time.

It is noted that pulses that are not expressly described herein as comprising microbeams may generally be provided as pulses having a cross-section with a single spatial local energy maximum (e.g. having a Gaussian cross-section), as opposed to pulses comprising microbeams, each microbeam providing its own spatial local energy maximum.

Notably, while the above steps of delivering the laser pulses are labelled as "first", "second", and "third", it is also within the scope of the invention that their order is interchanged (i.e., each of the three steps may be applied first, second and third, respectively).

It is also noted that the labels $p_1$, $p_2$, $p_{2a}$, $p_3$ and $p_4$ are used herein merely to make it easier to distinguish between the different types of pulses, similar to reference signs. It should be noted that certain types as described herein with reference to a certain label, e.g. $p_{2a}$, may fall within the scope of claimed pulses with a different label, e.g. $p_1$, as long as they have matching technical parameters.

The method may be repeated in desired intervals (ranging from weeks to months) to achieve optimal results. It may have a significant advantage over topical or oral combined pharmacological treatments, as the treatments are precisely localized, may avoid systemic effects and may not be dependent on patient compliance or the quality of the composition and application of the preparations.

Side effects of pharmacological therapies, which can be even more pronounced if several pharmacological therapies are combined, may possibly be avoided. However, it is also within the scope of the present invention to combine the described aspects based on laser pulses with pharmacological therapy. The duration and/or doses of the pharmacological therapy may thus be reduced compared to conventional approaches which may contribute to minimising side effects.

The relatively short pulses $p_1$ (e.g. high energy ultrashort laser pulses, or extremely short pulses in the nanosecond or picosecond range (ESP)) may be provided with parameters that are configured or optimized to cause selective photomechanical damage to excessive pigments concentrated in melanosomes without causing damage to the surface of the skin. These pulses may target excess melanin in the affected areas of the skin. They may also lighten or eradicate a variety of pigmented lesions. Presently preferred parameters of the pulses $p_1$ to which the scope of the present invention is not limited, however, are described hereinbelow.

It is the current understanding that relatively short laser pulses $p_1$ are effective because they confine their energy to the treated pigments. The time duration of these pulses is short enough that the pulse energy heats small pigment molecules to fragmentation temperature before their heat can dissipate to the surrounding skin. This prevents heating of the surrounding tissue that could potentially lead to burning or scarring of the skin. The relatively short laser pulses may be provided at relatively high-power such that the fragmentation temperature is reached within the relatively short pulse duration.

The relatively longer laser pulses $p_2$ of the second step may be provided with parameters configured or optimized to cause localized islets of mild hyperthermia below the skin surface resulting in the activation of tissue regeneration and reduction of inflammation. For example, a reduction in the production of cytokines and/or a control of the inherent inflammation in melasma may be achieved. The pulses $p_2$ may be longer than the relatively short laser pulses $p_1$ of the first step (e.g., the ESP pulses). For example, pulses $p_2$ may have a pulse duration in the microsecond to millisecond range. The pulses $p_2$ may be selected long enough to cause localized absorption and resulting heating in microscopic skin islets (e.g., melanosomes, skin imperfections, collagen bundles) achieving a reduction in the production of cytokines and control of the inherent inflammation in melasma. This causes the microscopic skin islets to heat up and to quickly transfer the heat to the surrounding tissue. As the heated islets are typically equally dispersed throughout the 3D volume of the tissue, regenerative anti-inflammatory response and connective tissue remodelling may thus be induced throughout the treated area. The pulses $p_2$ may, alternatively or additionally, be selected short enough to avoid bulk heating of tissue which is contraindicated in hyperpigmentation disorders, especially in higher Fitzpatrick skin types (IV-VI). Presently preferred parameters of the pulses $p_2$ to which the scope of the present invention is not limited, however, are described hereinbelow.

The laser pulses $p_3$ of the third step may be used to cause fractional microwounding (e.g. by fractional photothermolysis) of the epidermis of the skin, while leaving the other zones within the skin intact. The caused microdamage may induce tissue regeneration and keratinocyte turnover. Each microbeam of the laser pulses $p_3$ may lead to a microwound with a diameter corresponding to the diameter of the microbeam, whereas areas in between the microbeams may remain untreated (it is generally understood herein that the indicated diameters of (micro)beams and/or pulses relate to diameters of (micro)beams and/or pulses when they impinge onto the body of the patient, e.g. on the patient's skin). The untreated tissue, in return may trigger the regenerative processes which generally may lead to keratinocyte turnover and tissue renewal. This approach is gentle as the skin may heal much faster than if the whole area was treated, as the untreated tissue surrounding the treated zones helps to fill in the damaged area with new cells. Presently preferred parameters of the pulses $p_3$ to which the scope of the present invention is not limited, however, are described hereinbelow.

According to an aspect, each pulse of the pulses $p_1$ comprises a fluence from 0.1 J/cm$^2$ to 50 J/cm$^2$, preferably from 0.5 J/cm$^2$ to 10 J/cm$^2$. As used herein, the term fluence F is defined as F=E/A, wherein E is an energy of a laser pulse and A is the spot size area of the laser beam at the skin surface (e.g., the minimum surface in which 90% or at least 90% of the pulse energy is deposited).

According to a further aspect, each pulse of the pulses $p_1$ comprises a duration of at least 1 ps, preferably a duration from 10 ps to 100 ns. In an example, each pulse of the pulses $p_1$ comprises a duration from 1 ns to 10 ns. Pulse durations as described herein are generally understood as Full-Width-Half-Maximum (FWHM). However, in case of asymmetric pulses, these may also be understood as the minimum duration in which 90% of the pulse energy is delivered. The wavelength of pulses $p_1$ may, for example, be 1,064 nm, and the selected wavelength may depend on the depth within the skin of the elements to be treated, as will be outlined further below.

According to another aspect, each pulse of the pulses $p_2$ comprises a fluence from 1 $J/cm^2$ to 100 $J/cm^2$, preferably from 5 $J/cm^2$ $cm^2$ to 50 $J/cm^2$.

According to a further aspect, each pulse of the pulses $p_2$ comprises a duration of at most 10 ms, preferably a duration from 100 μs to 5 ms. The wavelength of laser pulses $p_2$ may be selected to penetrate relatively deeply through the skin surface (e.g. a wavelength of 1064 nm may be selected or any wavelength which provides a similarly deep penetration in human skin).

According to another aspect, each pulse of the pulses $p_3$ comprises a fluence from 1 $J/cm^2$ to 100 $J/cm^2$, preferably from 5 $J/cm^2$ to 50 $J/cm^2$.

According to yet another aspect, each pulse of the pulses $p_3$ comprises a duration from 0.1 ns to 100 ns, preferably a duration from 1 ns to 10 ns. Pulses $p_3$ may be provided with one or more wavelengths from a relatively wide range, e.g. from near infrared to far infrared (e.g. a wavelength of 1064 nm may be selected).

According to an aspect, each pulse of the pulses $p_1$ and/or each pulse of the pulses $p_2$ has a diameter from 1 mm to 20 mm, preferably from 2 mm to 8 mm.

According to a further aspect, each microbeam has a diameter of at least 10 nm, preferably a diameter from 50 μm to 800 μm. The microbeams may be configured such that the laser light of each pulse is delivered in an array of microbeams (e.g., an array of m×n microbeams, wherein m and n may range from 2 to 20, for example) producing dot- or pixel-like treated areas in the skin (e.g. by fractional photothermolysis or fractional laser resurfacing).

According to a further aspect, the described method may comprise the further step of delivering laser pulse $p_4$ onto the body, wherein each pulse of the laser pulses $p_4$ is configured to have a diameter of at least 100 μm and a duration of at least 0.1 ms. Presently preferred parameters of the pulses $p_4$ to which the scope of the present invention is not limited, however, are described hereinbelow.

In contrast to the pulses $p_3$ which comprise several microbeams such that the beam cross section comprises several local energy maxima, the pulses $p_1$ and $p_2$ may be configured to comprise a cross section having a single local energy maximum (e.g. a cross section that follows an approximate Gaussian profile). The cross section and/or diameter of the pulses $p_4$ may be configured similarly as those of pulses $p_1$ and $p_2$.

According to another aspect, each pulse of the pulses $p_4$ comprises a fluence from 10 $J/cm^2$ to 400 $J/cm^2$, preferably from 50 $J/cm^2$ to 200 $J/cm^2$ According to yet another aspect, each pulse of the pulses $p_4$ comprises a duration of at most 100 ms, preferably a duration from 10 ms to 60 ms.

According to a further aspect, the method further comprises the step of selecting a wavelength of the laser pulses $p_1$ as a function of a depth of the melasma and/or the related hyperpigmentation disorders within a skin of the patient. Thus, the energy of the laser pulses may be deposited in a range of depth suitable for treating the melasma and/or the related hyperpigmentation at its respective depth.

According to yet another aspect, the method may comprise the further step of applying a topical and/or systemic antioxidant treatment to the patient. By means of tackling the melasma and/or the related hyperpigmentation by laser pulses and topical and/or systemic antioxidant treatment, a particularly effective treatment may be provided. The topical and/or systemic antioxidant treatment may also be applied as a prophylactic treatment in order to prevent further oxidative damage and re-appearance of the hyperpigmentation condition.

A further aspect of the present invention relates to an apparatus for treating melasma and/or related hyperpigmentation disorders. The apparatus comprises a laser device having at least one laser source for generating laser pulses. It further comprises at least one control unit for controlling the laser device. The control unit is configured to cause the laser device to perform two or more of the following steps: According to a first step, laser pulses $p_1$ are delivered, wherein each pulse of the pulses $p_1$ is configured to have a diameter of at least 100 μm and a duration of at most 1 μs. According to a second step, laser pulses $p_2$ are delivered, wherein each pulse of the pulses $p_2$ is configured to have a diameter of at least 100 μm and a duration of more than 1 μs. According to a third step, laser pulses $p_3$ are delivered, wherein each pulse of the pulses $p_3$ is configured to comprise a plurality of microbeams, each microbeam having a diameter below 1 mm.

According to an aspect, the at least one laser source comprises only a single laser source. Hence, providing several laser sources may be avoided, which may help to provide the apparatus in a simple and cost-efficient manner.

According to a further aspect, the at least one control unit comprises only a single control unit and only a single laser device. The single control unit is integrated, together with the at least one laser source, into the single laser device. Hence, providing several control units and the need to coordinate them may be avoided. Instead, a single control unit provides the necessary control for the one or more laser sources.

According to an aspect, the laser device comprises an applicator configured to receive laser pulses generated by the at least one laser source and to deliver them onto a patient. The applicator may comprise a pulse geometry shaper suitable for shaping the geometry of the laser pulses directed onto the patient.

According to an aspect, the apparatus is configured for performing the method steps as described herein and/or the method steps described herein may be performed by the apparatus described herein.

A further aspect relates to a computer program product, comprising a computer-readable medium comprising code for causing at least one laser device for delivering laser pulses to perform two or more of the following steps: According to a first step, laser pulses $p_1$ are delivered, wherein each pulse of the laser pulses $p_1$ is configured to have a diameter of at least 100 μm and a duration of at most 1 μs. According to a second step, laser pulses $p_2$ are delivered, wherein each pulse of the laser pulses $p_2$ is configured to have a diameter of at least 100 μm and a duration of at least 1 μs. According to a third step, laser pulses $p_3$ are delivered, wherein each pulse of the laser pulses $p_3$ comprises a plurality of microbeams, each microbeam having a diameter below 1 mm.

In an aspect, the computer program product may be a part of the apparatus and/or the control unit as described herein.

4. BRIEF DESCRIPTION OF FIGURES

Figure 2A:
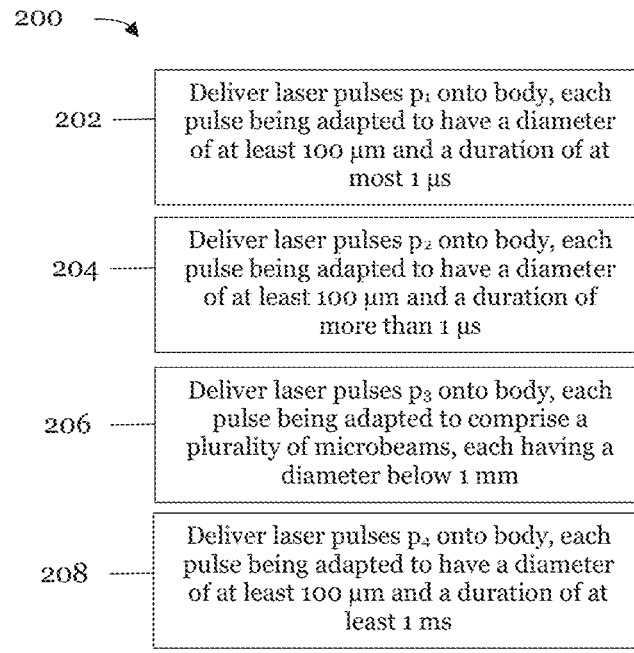
Figure 2B:
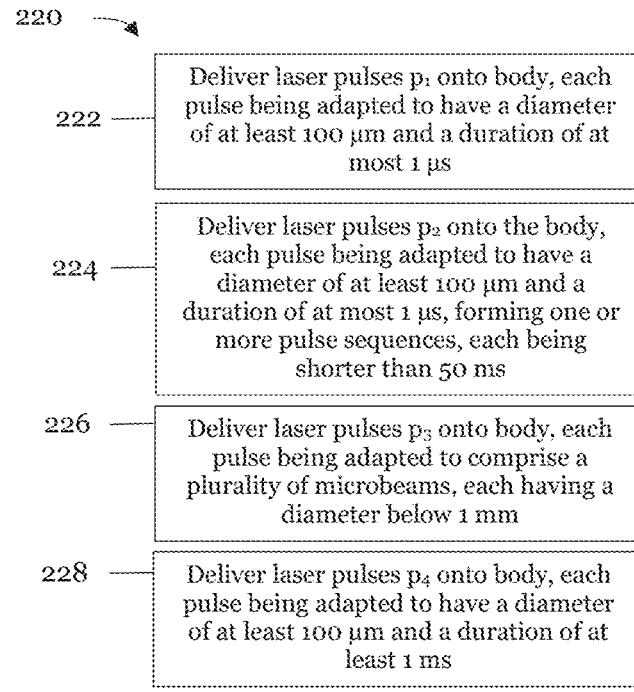
Figure 3:
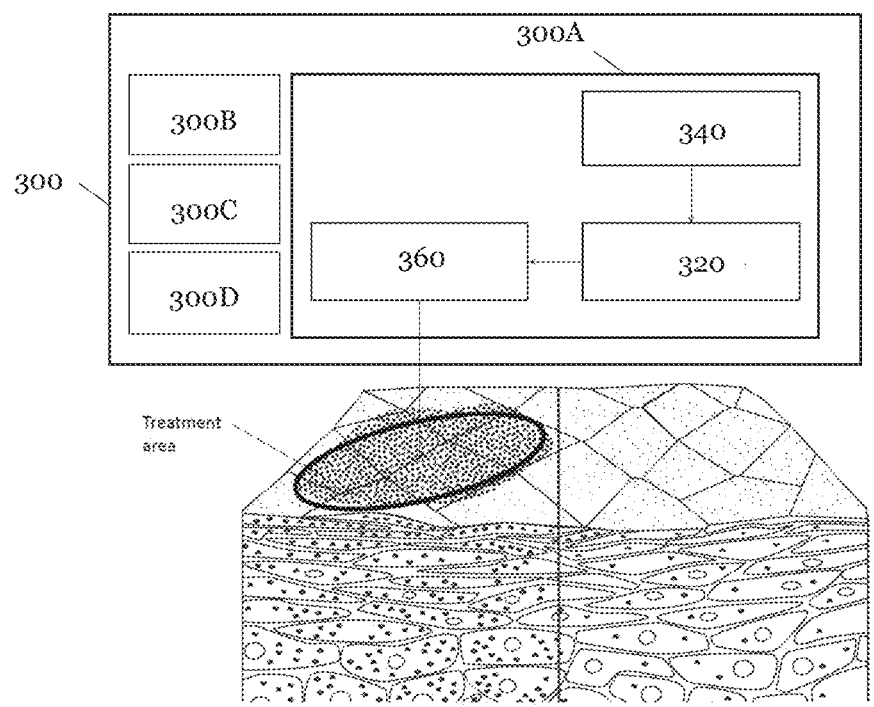
Figure 4:
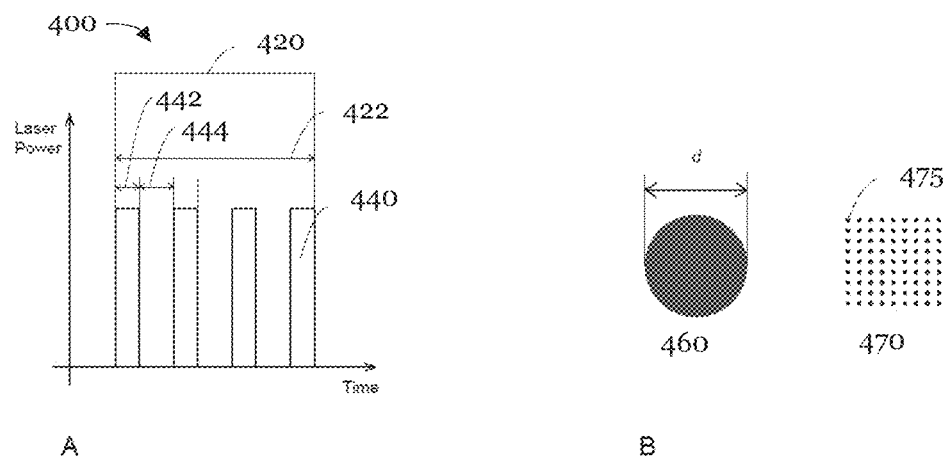
Figure 5A:
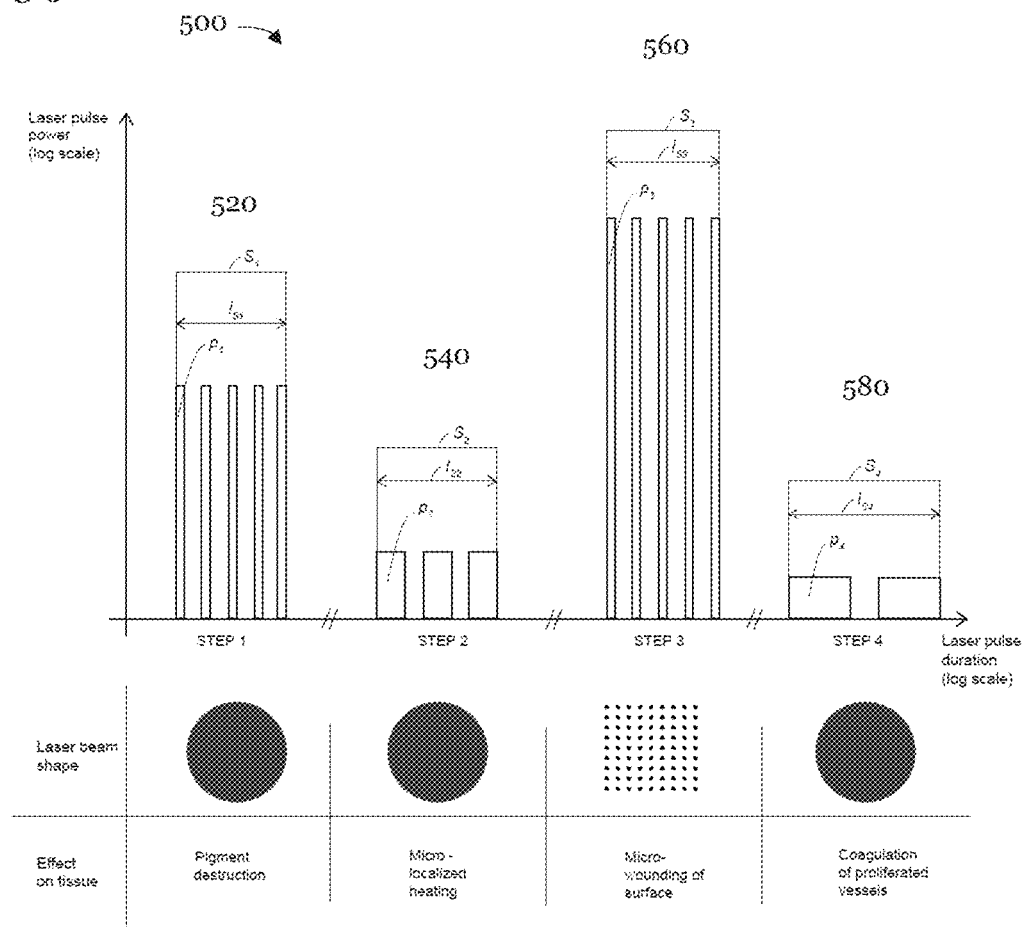
Figure 5B:
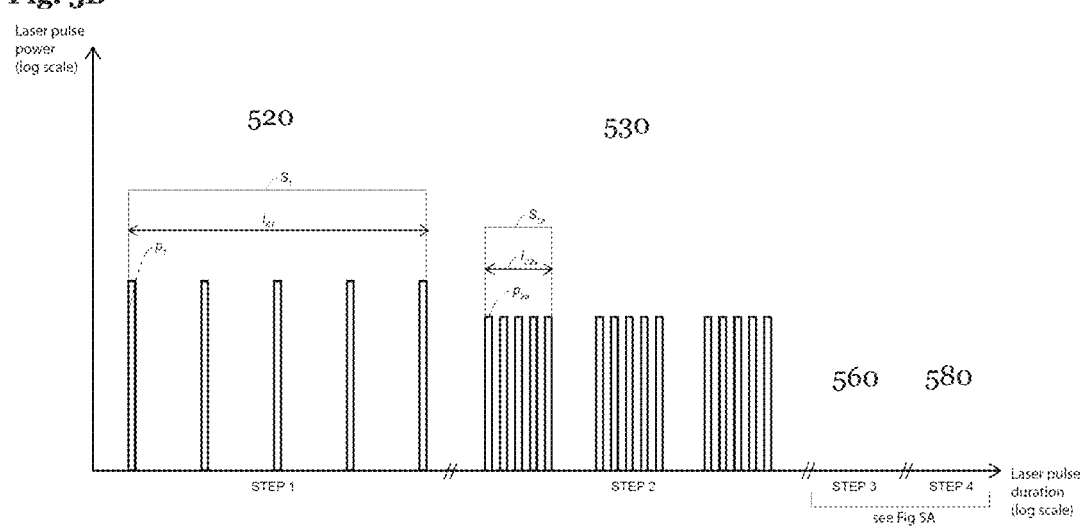

FIG. 1: Cross-sectional view of exemplary skin and exemplary cells contributing to hyperpigmentation;

FIG. 2A: Flow chart according to an exemplary method;

FIG. 2B: Flow chart according to a further exemplary method;

FIG. 3: Schematic illustration of an exemplary apparatus;

FIG. 4A: Schematic illustration of an exemplary pulse sequence, consisting of several laser pulses;

FIG. 4B: An illustration of two exemplary spatial profiles (cross-sections) of laser pulses;

FIG. 5A: A schematic illustration of exemplary pulse sequences; several subsequent steps of different laser pulsing modes are shown; laser beam profiles and tissue effects resulting from each step of the treatment are shown at the bottom of the illustration;

FIG. 5B: A schematic illustration of exemplary pulse sequences; several subsequent steps of different laser pulsing modes are shown.

5. DETAILED DESCRIPTION

FIG. 1 shows in a schematic cross-sectional view a hyperpigmented skin portion 11 (left side) and a normally pigmented skin portion 102 (right side). Skin portion 101 comprises a hyperpigmented area no. Typically, this is a more strongly coloured area on the surface, indicating a higher concentration of melanin in the skin below that area. Typically, the treatment area onto which the laser pulses described herein are applied covers hyperpigmented area no.

Hyperpigmented area no comprises a top epidermal layer, a lower dermis, and a dermis-epidermis junction in between. Undesired pigments are typically created by melanocytes 120 and transferred to keratinocytes 130 and are mainly located in the epidermis. Unwanted pigments can also be present in the dermis, e.g., inside melanophages 140, which are macrophages that have engulfed melanin by phagocytosis of either senescent cells or leaked melanosomes 180. In the dermis, hyperproliferation of blood vessels is also common in chronic hyperpigmentation disorders, such as melasma. The dermis is mainly composed of extracellular matrix 150, which is synthesised and excreted by fibroblasts 160 which are important mediators of regenerative and (anti)inflammatory processes. At the depth level of melanophages 140, extracellular matrix 150 and fibroblasts 160, generally also blood vessels 170 may be located.

FIG. 2A shows an exemplary method 200 for treating a treatment area comprising melasma and/or related hyperpigmentation disorders of a patient including steps 202, 204, 206, 208. It is emphasized that the steps may be performed in that order. However, the order of these steps may also be changed, and one or more steps may be omitted entirely. The treatment area may be the same in each step. However, it is noted that different treatment areas may be used in each step. For example, the treatment area may be selected to correspond to an area of the skin of the patient which suffers from melasma and/or related hyperpigmentation disorders. It may, however, in one or more steps also be selected to correspond to a larger area, e.g. if a portion of a part of the patient's body (e.g., a portion of a cheek) suffers from melasma and/or related hyperpigmentation disorders, e.g., the entire part of the patient's body (e.g., the entire cheek) or even a super-ordinate part of the body (e.g., the face) may be selected as treatment area.

In step 202, laser pulses $p_1$ are delivered onto the body, wherein each pulse of the laser pulses $p_1$ may be configured to have a diameter of at least 100 µm and a duration of at most 1 µs.

Each pulse of pulses $p_1$ may generally be configured to comprise a duration of at least 1 ps. They may also be configured to comprise a duration from 10 ps to 100 ns, from 100 ps to 100 ns, from 100 ps to 25 ns, or from 1 ns to 25 ns, or from 1 ns to 10 ns. Each pulse of pulses $p_1$ may generally be configured to comprise a fluence from 0.1 J/cm$^2$ to 50 J/cm$^2$. They may also be configured to comprise a fluence from 0.5 J/cm$^2$ to 10 J/cm$^2$, from 0.5 J/cm$^2$ to 5 J/cm$^2$, cm$^2$, or from 2 J/cm$^2$ to 10 J/cm$^2$.

For example, a laser source capable of generating ESP laser pulses may be used to generate pulses $p_1$. One of the techniques by which a laser source can be made to produce pulses $p_1$ is Q-switching (QS), sometimes known as giant pulse formation. The technique allows the production of light pulses with extremely short (e.g., in the range of pico- or nanoseconds) pulse duration and high (e.g., megawatt) peak power, much higher than can be produced by the same laser source operating in continuous wave mode (constant output), or free-running pulse mode (with pulse durations e.g. in the range from 0.1 ms to 300 ms). For example, ESP pulses may thus be provided.

The most likely cause of pigment destruction when subjecting the pigments to pulses $p_1$ are shockwave and/or cavitation damage, the photomechanical physical effects produced from thermal expansion, and/or the extreme temperature gradients created within the melanosome. Melanin may absorb and localize the high-intensity radiation, thereby creating a sharp temperature gradient between the melanosome and surrounding structures. This gradient leads to thermal expansion and the generation and propagation of acoustic waves, which mechanically damage the melanosome-laden cells.

For the selective removal of pigments, the wavelength of laser pulses $p_1$ may be selected such that the laser light of laser pulses $p_1$ penetrates far enough into the skin to reach the target pigments and/or is highly absorbed by the pigments relative to the surrounding skin. Various wavelengths may be used for that matter, e.g. for specifically targeting pigmented lesions. For example, wavelengths of red color (e.g., 694 nm as obtainable from a ruby laser source, or 755 nm from an alexandrite laser source), green color (e.g., 532 nm obtainable from a frequency-doubled Nd:YAG laser source or a potassium titanyl phosphate KTiOPO$_4$ (KTP) laser source), and/or near-infrared wavelength (e.g., 1,064 nm obtainable from a Nd:YAG laser source).

In some examples, method 200 comprises the step of selecting the wavelength of pulses $p_1$ as a function of the depth within the skin at which the pigments to be removed (or other targeted elements) are located. For example, for superficially located pigments (or elements) shorter wavelengths are selected, whereas for removal of deeper pigment longer wavelengths are selected, as these generally penetrate to greater tissue depths. For example, wavelengths of green color do not penetrate as deeply into the skin as wavelengths in the red and near-infrared range because of their shorter wavelengths. Hence, a wavelength of green color may be selected for pigments that are located relatively superficially, e.g., epidermal pigmented lesions.

For example, a Q-switched Nd:YAG, a Q-switched ruby, and/or a Q-switched alexandrite laser source may be used as a laser source for pulses $p_1$ (e.g., ESP pulses). The infrared wavelength provided by a Nd:YAG laser source is typically not absorbed as well by melanin as, e.g., green or red wavelengths. However, its advantage lies in its ability to penetrate more deeply into the skin (up to 4 mm to 6 mm) such that it is capable to destroy even hard to treat pigments deposited in melanophages in the dermis. It is also more useful in the treatment of lesions for individuals with darker skin tones. Hence, it may presently be preferred to use a Q-switched Nd:YAG laser source for pulses $p_1$.

In some examples, pulses $p_1$ can be delivered in pulse sequences $S_1$. Each sequence $S_1$ may have a number $n_1$ of pulses $p_1$, with a time in between two subsequent pulses of $t_1$, with a pulse sequence repetition rate (pulse sequences per second) $f_1$ and the total duration of a sequence (sequence length) $l_1$. The number $n_1$ may be selected e.g. from 2 to 50, but also between 2 and 20. The time $t_1$ may be selected from 1 µs to 10 ms, e.g., from the range 200 µs to 5 ms or 500 µs to 2 ms. The pulse sequence repetition rate $f_1$ can be selected in the range from about 0.1 to about 100 pulse sequences per second, 0.5 to 20 pulse sequences per second, or 1 to 10 pulses sequences per second. Similarly, the pulse repetition rate can be selected in the range from about 0.1 to about 100 pulses per second, 0.5 to 20 pulses per second, or 1 to 10 pulses per second. The sequence length $l_1$ depends on $n_1$ and $t_1$, and may be selected, e.g., from the range 0.1 ms to 50 ms, or 0.5 ms to 10 ms, or 2 to 8 ms.

Each pulse of pulses $p_1$ may be configured to have a diameter from 0.1 mm to 20 mm, 1 mm to 10 mm, or from 2 mm to 8 mm, for example.

In step 204 of the preferred embodiment, laser pulses $p_2$ are delivered onto the body, wherein each pulse of the laser pulses N is configured to have a diameter of at least 100 µm and a duration of more than 1 µs.

Generally, the same wavelengths and/or laser sources may be used for pulses $p_2$ as described above for pulses $p_1$. However, pulses $p_2$ may be adjusted to comprise longer pulse durations, e.g. from 1 µs up to 1 s. For example, each pulse of the pulses $p_2$ may be configured to comprise a duration from 1 µs to 100 ms, or from 10 µs to 100 ms, or from 100 µs to 100 ms, or 100 µs to 10 ms, or from 100 µs to 5 ms, or from 200 µd to 2 ms. Moreover, each pulse of the pulses $p_2$ may be configured to comprise a fluence from 1 $J/cm^2$ to 100 $J/cm^2$, or from 2 $J/cm^2$ to 50 $J/cm^2$, or from 5 $J/cm^2$ to 50 $J/cm^2$ or from 10 $J/cm^2$ to 50 $J/cm^2$.

Pulses $p_2$ may comprise a lower pulse peak power than pulses $p_1$, resulting in a photothermal effect on the tissue. Pulses $p_2$ may be precisely adjusted in their duration as described herein.

Pulses $p_2$ may also be configured to comprise a wavelength that has a higher skin penetration depth than that selected for pulses $p_1$. Thus, localized absorption and heating of microscopic skin targets inside the treatment volume may be achieved.

The described approach is possible due to the concept of selective photothermolysis, which is described in more detail further below.

Upon irradiation of tissue with a suitable short laser pulse, energy is deposited in the absorbing structure before much heat can be transferred to the surrounding tissue by conduction. The resulting temperature rise in an optically and thermally homogenous structure is thus directly proportional to the absorbed heat, which is in turn proportional to the laser fluence in the target. In general, however, a significant fraction of the deposited heat may diffuse away from the absorbing structure during laser exposure, which reduces the peak target temperature and impairs the spatial selectivity of the heating, even if the wavelength provides selective absorption of laser energy. Therefore, selection of laser pulse duration, which determines the spatial confinement of deposited heat in absorbing structures, preferably should be done in an optimal manner. Only laser pulses durations that are significantly shorter than the target thermal relaxation time T enable a maximal temperature rise in the targeted structure. Otherwise, the heat deposited locally during the (relatively long) pulse duration will flow also to the surroundings, such that the local temperature will not be maximal. Here, the relaxation time T represents the time interval in which the amplitude of a hypothetical temperature rise decreases by approximately a factor of 2 (due to, e.g., the diffusion of heat into surrounding tissue). Notably, a typical thermal relaxation time T of human skin is in the range from 10 ms to 50 ms.

Especially with wavelengths that penetrate more deeply into the tissue, selective tissue modification can be achieved by adjusting the laser pulse duration to the thermal relaxation time of the targeted subcellular islets of skin. A suitably short laser pulse confines the heating effect to the subcellular islets in the skin, resulting in maximum temperature difference between the target and adjacent structures. Short pulse durations maximise the thermal effect in the absorbing skin islets (e.g., pigments containing organelles, microvessels, imperfections, etc.), while minimising the temperature diffusion to the neighbouring tissue. Size-dependent targeting of microscopic skin islets causes them to heat-up, causing a temperature gradient and subsequent heat transfer between the targets and the surrounding tissue. This approach creates heat pulses distributed in a fractional manner or like a mosaic below the skin surface. For example, the duration of pulses may be selected as a function of the size of one or more targeted elements. For example, for relatively large melanophages, a longer duration may be selected.

For example, it is a presently preferred example to use a Nd:YAG laser source for pulses $p_2$. In this example, it may be preferred to select pulse durations from 100 µs to 100 ms (but also any other of the ranges specified herein may be used). Short pulses of Nd:YAG laser light, which penetrate relatively deeply through the skin surface, may selectively be absorbed in microscopic skin islets below the skin surface, which causes them to heat up and quickly transfer the heat to the surrounding tissue. As the heated islets are equally dispersed throughout the 3D volume of the tissue, regenerative anti-inflammatory response and connective tissue remodelling is induced throughout the treated area.

Also pulses $p_2$ may be delivered in sequences $S_2$ of pulses. The repetition rate $f_2$ is for example, 0.1 to 100 pulse sequences per second, or 0.5 to 10 pulse sequences per second, or 1 to 5 pulse sequences per second. However, the pulses may also be delivered without separating them into pulse sequences. For example, 0.1 to 100 pulses may be delivered per second, or 0.5 to 10 pulses per second, or 1 to 5 pulses per second.

Each pulse of the pulses $p_2$ may be configured to have a diameter from 0.1 mm to 20 mm, 1 mm to 10 mm, or from 2 mm to 8 mm, for example.

In step 206, laser pulses $p_3$ are delivered onto the body, wherein each pulse of the laser pulses $p_3$ comprises a plurality of microbeams, each microbeam having a diameter below 1 mm.

Such micropunctures or microwounding by high energy laser pulses in focused microbeams, may stimulate overall anti-inflammatory response in the treated skin, promote keratinocyte turnover, stimulating keratinocyte to fibroblast paracrine signalling, induce regenerative processes in the skin and resulting renewal of tissue.

Apart from the specific parameters described herein for pulses $p_3$, pulses $p_3$ may generally be configured to also comprise parameters relating to their pulse duration, fluence and/or delivery in one or more sequences as outlined above with reference to pulses $p_1$. However, the laser light or laser energy is delivered to the treated area in the form of microbeams (e.g., forming several pixels). Thus, the skin exposed to the microbeams may be microwounded, whereas the skin in between microbeams (which may be a larger portion than the skin exposed to the microbeams) may remain intact.

For example, pulses $p_3$ may be generated by a Q-switched Nd:YAG laser source and then delivered in a fractioned manner. Preferably, temporally short ESP pulses are used with an energy that is high enough to cause surface ablation of the treated microspots due to the pulses photoacoustic effect. Although the Nd:YAG wavelength is usually considered as non-ablative, very high energies delivered in ultra-short pulses in micro-sized beams can also cause surface microwounding of the skin.

For example, pulses $p_3$ can be delivered in pulse sequences $S_3$, having a number $n_3$ of pulses, with a time in-between pulses $t_3$, a pulse sequence repetition rate $f_3$ and sequence length $l_3$. The number $n_3$ can vary and is preferably between 2 and 50, or 2 and 20. The sequence length $l_3$ may vary from 0.1 ms to 100 ms, presently preferred from 0.5 ms to 10 ms. The distance between pulses in a pulse sequence $t_3$ may be in the range from 10 µs to 10 ms, e.g. (presently preferred) 100 µs to 5 ms, but also 200 µs to 2 ms. Repetition rate $f_3$ may be selected to be from 0.1 to 100, 0.5 to 100, or 0.5 to 50 pulse sequences per second. Similarly, also the number of pulses may be selected (with or without grouping pulses into sequences) from 0.1 to 100, 0.5 to 100, or 0.5 to 50 pulses per second Each pulse $p_3$ may generally be configured to provide micropunctures on the treated surface. Each individual microbeam of the pulses $p_3$ may be configured to comprise a fluence from 5 J/cm² to 100 J/cm², from 5 J/cm² to 10 J/cm², from 10 J/cm² to 100 J/cm², or from 10 J/cm² to 50 J/cm². Moreover, each pulse of the pulses $p_3$ may be configured to comprise a duration from 0.1 ns to 100 ns, from 1 ns to 100 ns, from 0.1 ns to 10 ns, or a duration from 1 ns to 10 ns. Each microbeam of the pulses $p_3$ may be configured to comprise a diameter of at least 10 µm, for example a diameter from 50 µm to 800 µm, or from 100 µm to 500 µm.

For pulses $p_3$, in some examples, a wavelength is used that differs from that used for pulses $p_1$ and/or $p_2$. For example, wavelengths that range from approximately 2 µm to 11 µm may be used. These have relatively high water absorption and are consequently almost completely absorbed on the tissue surface. Hence, these may be used to create a microwounding effect on the tissue surface without significantly affecting lower tissue layers. When the fluence of laser pulses $p_3$ is increased to reach values above the skin ablation threshold, the surface of the skin is vaporized or ablated. The depth of ablation increases with increasing fluence.

In some examples, an Er:YAG laser is used as a laser source (providing a wavelength of 2940 nm) for pulses $p_3$. In a presently preferred example, a per pulse fluence between 5 J/cm² and 50 J/cm² is used.

In other examples, pulses $p_3$ may also be provided such that they do not provide an ablation on the skin surface. For example, Er:YAG laser pulses or pulse sequences can be delivered in a recently described dual tissue regeneration mode, as described in European patent application EP 18172363 which is incorporated by reference herein. This mode consists of very short laser pulses or pulse sequences that create a non-ablative thermal "needling" (i.e., triggering) effect, with pulses so short that the laser pulse delivery time and the temperature diffusion time combined are shorter than 900 microseconds. In this embodiment, both fractional as well as full laser beams can be used.

In some examples, additionally or alternatively to step 206, microwounding of the skin may be achieved in another way, for example by using mechanical methods, such as using microneedles or other electro-magnetic sources such as incoherent light sources or radiofrequency. Acoustic means, such as ultrasound, may also be used.

In step 208, laser pulses $p_4$ are delivered onto the body, wherein each pulse of the laser pulses $p_4$ is configured to have a diameter of at least 10 nm and a duration of at least 1 ms.

For example, each pulse of the pulses $p_4$ may be configured to comprise a fluence from 10 J/cm² to 400 J/cm², from 50 J/cm² to 400 J/cm², from 10 J/cm² to 200 J/cm², or from 50 J/cm² to 200 J/cm². Each pulse of the pulses $p_4$ may be configured to comprise a duration in the range from 0.1 ms to 300 ms, 0.1 ms to 100 ms, from 1 ms to 100 ms, or from 10 ms to 60 ms.

Pulses $p_4$ may be applied to target hyperproliferated blood vessels, with laser pulse duration and energy selected to target superficial vessels in melasma-affected areas (such as vessels 170 described with reference to FIG. 1). For example, the fluence is adjusted to be high enough to cause high absorption in haemoglobin, leading to heating and coagulation of the microvessels (and thus destruction and reduction in their appearance). To optimize absorption, wavelengths that are relatively strongly absorbed by haemoglobin may be selected.

In a presently preferred example, an Nd:YAG laser source in free-running pulse mode may be used (with pulse durations e.g. in the range from 0.1 ms to 300 ms). A duration of such laser pulses $p_4$ from 10 to 60 milliseconds may particularly be beneficial to achieve selective photothermolysis in such a way to maximize the temperature rise in the vessels and minimize the heat diffusion in the surrounding surface during the laser pulse, causing their coagulation. A fluence in the range from 50 to 200 J/cm² may be selected accordingly. However, also other wavelengths and correspondingly other laser source may be used for pulses $p_4$, e.g., those as described above with reference to pulses $p_1$, $p_2$, $p_3$.

Particularly, during step 208, surface cooling of the skin may be utilized. However, also steps 202, 204, and 206 may be accompanied by surface cooling of the skin.

In some embodiments, additionally or alternatively to step 204, shorter pulses than 1 µs may be delivered (as generally defined with respect to pulses $p_1$) that, e.g., comprise a pulse duration from 1 ps to 50 ns (e.g. by using ESP pulses, e.g., provided by a Q-switched Nd:YAG laser source). These are then grouped in a pulse sequence $S_{2a}$, with time in-between pulses $t_{2a}$ and pulse sequence length $l_{2a}$ adjusted in such a way to achieve slight heating pulses of the treated area, e.g. a similar effect as described above with respect to pulses $p_2$.

If the pulse sequence length $l_{2a}$ is shorter than the thermal relaxation time (e.g., shorter than 10 ms or shorter than 50 ms) but the pulse sequence comprises several pulses with durations in the nanosecond range, even these short pulses can lead to localized heat diffusion from the absorption target into the surrounding area. In this way, extremely small targets and areas around these are heated up in sequential extremely short heat shocks. The result is a steep heat gradient and resulting quick heat transfer onto the surrounding surface. This localized heating effect is amplified by having more pulses in a pulse sequence closely spaced together, so that the heat does not completely diffuse between pulses, as the pulse sequence length $l_{2a}$ is shorter or equal to the thermal relaxation time of human skin. Such high frequencies of ESP pulses have previously been difficult to achieve using solid state Q-switched lasers, and therefore the use of high frequency Q-switched pulses in medicine is limited, which presents another novel feature of the present inventive method. For example, the number of pulses in each pulse sequence may be selected from 2-50, and it is presently preferred to be in the range from 2 to 20. A suitable corresponding sequence length is in the range from 1 ms to 50 ms and the preferred time in-between pulses $t_{2a}$ in the range from 100 is to 2 ms. The time between two subsequent pulse sequences may range from 50 ms to 100 ms, or it may be even more. In this alternative, the cumulative fluence of the pulses $p_{2a}$ within the pulse sequence $S_{2a}$ may be equivalent to the cumulative fluence for the above described longer pulses $p_2$. The pulse repetition rate inside the sequence may be configured to be in the range from 100 pulses per second to 10000 pulses per second, or in the range from 500 pulses per second to 7000 pulses per second or in the range from 1000 to 5000 pulses per second.

In some embodiments of the invention, the fluence of the individual pulses $p_{2a}$ may be equivalent to the fluence of pulse $p_1$ from the first step. In this case, a combined effect of melanosome disruption and localized heating due to high pulse repetition within pulse sequences would be achieved. In this embodiment, step 202 could be omitted.

In other embodiments of the invention, the fluence of the individual pulses might be lower than the fluences of the pulses $p_1$ from the first step, achieving only a heating effect surrounding nano-sized absorbing targets e.g. pigments and melanosomes. In this embodiment, the heating effects achieved are similar as with as pulses $p_2$, with the difference that the absorbing targets of pulses pea are smaller and thus more dispersely distributed.

In other embodiments of the invention, other non-ablative laser techniques can be used additionally or alternatively to step 204 which can create non-ablative micro-localized heating effects in the skin.

FIG. 2B shows an exemplary method 220 for treating a treatment area comprising melasma and/or related hyperpigmentation disorders of a patient including steps 222, 224, 226, 228. It is emphasized that the steps may be performed in that order. However, the order of these steps may also be changed, and one or more steps may be omitted entirely. The treatment area may be the same in each step. However, it is noted that different treatment areas may be used in each step. For example, the treatment area may be selected to correspond to an area of the skin of the patient which suffers from melasma and/or related hyperpigmentation disorders. It may, however, in one or more steps also be selected to correspond to a larger area, e.g. if a portion of a part of the patient's body (e.g., a portion of a cheek) suffers from melasma and/or related hyperpigmentation disorders, e.g., the entire part of the patient's body (e.g., the entire cheek) or even a super-ordinate part of the body (e.g., the face) may be selected as treatment area.

Optional step 222 can generally be implemented in the same or a similar manner as outlined above with respect to pulses $p_1$ of step 202 and reference to FIG. 2A.

In step 224, laser pulses $p_2$ are delivered onto the body, wherein the pulses may be configured to form one or more pulse sequences with pulse sequence lengths shorter than the thermal relaxation time (e.g., shorter than 10 ms or shorter than 50 ms).

Each pulse sequence may comprise several pulses with durations in the nanosecond range, i.e. <1 μs. In this scenario, even these short pulses can lead to localized heat diffusion from the absorption target into the surrounding area. Such high frequencies of ESP pulses (with, e.g., megawatt peak power) have previously been difficult to achieve using solid state Q-switched lasers, and therefore the use of high frequency Q-switched pulses in medicine was limited previously.

Each pulse of the laser pulses $p_2$ may be configured to have a diameter of at least 100 μm and/or a duration of at most 1 μs, e.g. a pulse duration from 1 ps to 50 ns (e.g. by using ESP pulses, e.g., provided by a Q-switched Nd:YAG laser source). These may then be grouped in a pulse sequence $S_2$, with a pulse sequence length $l_2$ and various other parameters (such as, but not limited to: number of pulses in each pulse sequence; time in-between pulses $t_{2a}$, time between two subsequent pulse sequences; cumulative fluence; pulse repetition rate inside the sequence; fluence of the individual pulses). Generally, the same parameters, as outlined above with reference to pulses $p_{2a}$ and pulse sequences $S_{2a}$ with reference to FIG. 2A, may be used. In particular, if the fluence of pulses $p_2$ is selected to be in the ranges described above with respect to pulses $p_1$ referring to step 202 of FIG. 2A, step 222 of FIG. 2B may be omitted.

In other embodiments of the invention, other non-ablative laser techniques can be used additionally or alternatively to step 224 which can create non-ablative micro-localized heating effects in the skin.

In step 226 and optional step 228, further pulses are delivered onto the body. These steps can be implemented just as described with reference to steps 206 and 208 of FIG. 2A.

FIG. 3 shows a schematic illustration of an exemplary apparatus 300. Apparatus 300 comprises a laser device 300A for treating a treatment area on skin of a patient. Apart from laser device 300A, the apparatus may also comprise further parts, e.g. a system 300B for cooling the treatment area (e.g., by means of a nozzle that directs a cooling agent onto the treatment area, e.g., a cooled gas, e.g., cooled air) and/or an image acquisition system 300C.

Laser device 300A comprises a laser source 320 for generating laser pulses (although only a single laser source 320 is depicted, it is understood that also two or more laser sources 320 may be provided in apparatus 300 and/or in laser device 300A).

Apparatus 300 further comprises a control unit 340 for controlling the laser device. In FIG. 3, control unit 340 is part of the laser device 300A. However, in other examples, control unit 340 may also be provided external to laser device 300A. For example, control unit 340 may be a processor, a computer, etc., which comprises a suitable interface to control laser source 320 and/or other components of laser device 300A.

Control unit 340 may provide a user interface by means of which the user can select the parameters of the pulses and/or pulse sequences to be delivered, as described herein. The user interface may be configured such that the user can directly enter the mentioned parameters. However, it may also be configured such that the user enters different parameters (e.g. depth and size of region to be treated in each of the various steps as described herein; condition to be treated; patient skin type; etc.). Control unit 340 may then determine the parameters of the corresponding pulses and/or pulse sequences as a function of the entered parameters (e.g. depth and size of region to be treated; condition to be treated; patient skin type; etc.). For example, it may implement the step of selecting a wavelength of the laser pulses $p_1$, $p_2$ and/or $p_4$ as a function of a depth of the (region of the) melasma and/or the related hyperpigmentation disorders within the skin that is to be treated in each step, respectively.

In some examples, apparatus 300 may also comprise an image acquisition system 300C for acquiring images of the patient's skin. Image acquisition system 300C may comprise one or more cameras, sensitive to visible and/or infrared light. Apparatus 300 may be configured to provide an analysis of such images and to output a corresponding treatment area (size) and/or laser parameters to be used. This functionality may be implemented in control unit 340, for example, or a separate hardware, processor and/or computer, etc. may be provided for that purpose.

In some examples, apparatus 300 also comprises a temperature-sensing element (temperature sensor) 300D in order to monitor the surface temperature of the treatment area. Temperature sensing element 300D may work in a non-contact fashion, e.g. based on an infrared sensor, but it may also work in contact with the skin. For example, temperature sensing element 300D may be provided as a separate unit, it may be integrated in an applicator 360 of apparatus 300 (described further below) or it may be a part of image acquisition system 300C. Apparatus 300 may be configured to give a warning sign if the sensed temperature exceeds a predetermined threshold. Also, a feedback mechanism may be implemented to switch off laser device 300A in that case. Additionally or alternatively, a feedback loop may be implemented to adapt the fluence and/or number of pulses delivered by laser device 300A such as to achieve a certain temperature.

Laser device 300A further comprises an applicator 360 which receives laser pulses generated by the laser source 320 and directs them onto the treatment area. For example, the laser pulses maybe provided from laser source 320 to the applicator 360 by means of an optical cable (e.g., an elongated member that carries the laser pulses) which may include one or more optical fibers, and/or any other suitable means. Applicator 360 may comprise a handpiece which may be handheld to direct the laser pulses onto the desired treatment area. Moreover, applicator 360 may comprise an arrangement of one or more mirrors and/or lenses (e.g. integrated into the handpiece), to direct and/or focus the pulses onto the skin. Applicator 360 may be configured to be placed onto the skin of a patient such that, in that position, the pulses are correctly focused onto the skin.

Applicator 360 may be configured for manual movement across the treatment area. Additionally or alternatively, applicator 360 may be configured such that the pulses and/or pulse sequences are automatically distributed and/or scanned across the treatment area, e.g., as controlled by control unit 340. Applicator 360 may, for example, comprise movable mirrors to scan the pulses across the treatment area.

Applicator 360 may also comprise means for shaping the geometry of the laser pulses directed onto the patient, for example a pulse geometry shaper (e.g. integrated into the handpiece). The pulse geometry shaper may be provided in the form of an element with two or more transparent portions. These transparent portions may be dimensioned such that a pulse received by the applicator (which may have, e.g., a Gaussian shape) is shaped into a plurality of microbeams. For example, the element with two or more transparent portions may comprise a plate which is generally non-transparent to the laser pulses but has holes and/or areas with transparent material, such that microbeams are formed by those portions of the pulses that penetrate the holes and/or areas with transparent material. In other examples, other means may be provided to shape the geometry of the laser pulses, e.g. micro-mirrors, micro-lenses, etc. The means for shaping the geometry of the laser pulses directed onto the patient and/or the pulse geometry shaper may be configured such that it can be controlled by control unit 340. Hence, control unit can switch from delivery of microbeams to delivery of a regular (e.g., Gaussian) beam without any manual changes to applicator 360. In other examples, different applicators 360 may be used for that purpose. In still another example, the means for shaping the geometry of the laser pulses directed onto the patient and/or the pulse geometry shaper may be provided as a changeable part of applicator 360 such that it can simply be exchanged, e.g. by a surgeon.

Apparatus 300 may generally be configured to implement the methods as described herein. In particular, it may comprise a single laser device 300A with a single laser source 320 and a single control unit 340, wherein the single control unit 340 controls the laser pulse parameters delivered by single laser device 300A such as to implement any of the methods as described herein (in some examples, for microbeam generation a manual intervention may be foreseen, as described above). For example, a Nd:YAG laser source may be used.

In some examples, apparatus 300 may comprise a single laser device 300A containing two or more laser sources 320 (particular to implement the methods as described herein which require different wavelengths). For example, an Er:YAG and a Nd:YAG laser source may be contained. For example, in the first, second and fourth steps (e.g., steps 202, 204, 208 of FIG. 2A) as described herein, pulses generated by the Nd:YAG laser source may be used. For example, in the third step (e.g., step 206 of FIG. 2A), pulses generated by the Er:YAG laser source may be used. Also in these examples, it is within the scope of the invention that the apparatus may include only a single control unit 340 that controls the two or more laser sources 320, and in particular the parameters of the pulses generated by these. However, also each laser source 320 may comprise its own control unit 340.

FIG. 4A shows a diagram 400 of the power delivered by a sequence 420 of exemplary laser pulses 440 over time. Exemplary sequence 420 consists of four laser pulses 440. However, it is to be understood that any other number of laser pulses could be used. Pulse sequence 420 comprises a pulse sequence length 422. Each pulse 440 comprises a pulse duration 442, and pulses 440 are separated by a time 444. It is noted that the temporal shape of the pulses is shown as rectangular in FIG. 4A for ease of illustration. It is understood that any other temporal pulse shape may be used instead.

FIG. 4B shows an illustration of two exemplary cross-sections of laser pulses as used herein. Cross-section 460 is approximately circular and comprises a diameter of d. For example, pulses having a diameter d of 0.1 mm or more, as generally described herein, may be used. Such pulses may have an approximately Gaussian energy profile and the diameter may be defined as the diameter of the minimum area around the energy profile which comprises 90% of the pulse energy. In other examples, however, other profiles may be used, e.g., non-Gaussian, such as flat-top, etc., circular profiles but also non-circular profiles. Cross-section 470 is that of an exemplary fractioned pulse having a plurality of microbeams 475. In this example, the pulse comprises an approximately rectangular array of 9×9 microbeams.

However, in other examples, other arrangements of microbeams may be used. Microbeams may generally have dimensions as described herein, wherein the total extension of the fractioned pulse may have a diameter that is similar to those as described herein with reference to non-fractioned pulses.

FIG. 5A is a schematic representation 500 of exemplary sets of pulses $p_1$, $p_2$, $p_3$, $p_4$ delivered one after another in a first step 520, second step 540, third step 560, and in a fourth step 580, respectively. For example, all sets of pulses may be delivered by a single Nd:YAG laser source. Similarly as in FIG. 4A, the power delivered by the sets of pulses is shown over time. Notably, however, the power is indicated on a logarithmic scale. Moreover, below the time axis, the respectively used pulse cross-section is indicated as well as the intended effect of the pulses on the tissue. It is noted that the number of pulses and their temporal separation, duration, power and shape, shown in each of steps 520, 540, 560, 580 is only exemplary and any other parameters as broadly described herein could be used.

In the example of FIG. 5A, pulses $p_1$ and $p_3$ delivered in steps 520 and 560 approximately comprise the same pulse duration and temporal spacing in between pulses. However, pulses $p_3$ are delivered in form of pulses having a plurality of microbeams (e.g., as described with reference to FIG. 4B). Moreover, pulses $p_3$ are provided with a markedly higher peak power compared to pulses $p_1$. This may be attributed to the fact that pulses $p_3$ are mainly foreseen to provide microwounding of the surface, which requires a higher power, than the intended purpose of pulses $p_1$ that is pigment destruction (e.g., if the pulse duration is kept constant as well as the wavelength compared to pulses $p_1$).

In contrast, pulses $p_2$ delivered in step 540, comprise a markedly longer pulse duration than pulses $p_1$ and pulses $p_3$. At the same time, pulses $p_2$ comprise yet again lower peak power than pulses $p_1$ and $p_3$. However, due to their longer duration, the total fluence delivered by each pulse $p_2$ in the example of FIG. 5A may be similar than that provided by each pulse $p_1$. Generally, pulses $p_2$ are configured according to their intended purpose of micro-localized heating. Pulses $p_2$ may have the same laser beam shape or cross-section as pulses $p_1$.

Finally, pulses $p_4$ delivered in step 580 comprise yet lower peak power than pulses $p_2$. Also pulses $p_4$ comprise an even longer pulse duration than pulses $p_2$. This is again due to their specific intended purpose of coagulating proliferated vessels. It is noted that, due to their longer duration, the total fluence delivered by each pulse $p_4$ in the example of FIG. 5A may be similar than that provided by each pulse $p_2$, despite the lower peak power of pulses $p_4$. Pulses $p_4$ may again have the same laser beam shape or cross-section as pulses $p_1$.

FIG. 5B is a schematic representation 501 of exemplary sets of pulses $p_1$, $p_{2a}$, $p_3$, $p_4$ delivered one after another in a first step 520, second step 530, third step 560, and in a fourth step 580, respectively. For example, all sets of pulses may be delivered by a single Nd:YAG laser source. Similarly as in FIG. 5A, the power delivered by the sets of pulses is shown over time. Notably, steps 520, 560 and 580 may be identical to the steps outlined with reference to FIG. 5A using the same reference numbers (the pulses of steps 560 and 580 are not shown in FIG. 5B). Regarding pulses $p2a$ of step 530, it is also noted that the number of pulses and their temporal separation, duration, power and shape, shown in FIG. 5B is only exemplary, and any other parameters as broadly described herein, e.g. for pulses $p_{2a}$ of FIG. 2A and/or for pulses $p_2$ of FIG. 2B, could be used.

Notably, pulses $p_{2a}$ delivered in step 530, may be delivered in a number of pulse sequences $S_{2a}$ that comprise a shorter pulse spacing than used for pulses $p_1$, $p_3$ and/or $p_4$. Pulses $p_{2a}$ may comprise lower peak power than pulses $p_1$, $p_3$ and/or $p_4$. However, this is only optional. Pulses $p_{2a}$ may have the same laser beam shape or cross-section as pulses $p_1$.

Those of skill in the art will appreciate that the various illustrative logical blocks, modules, circuits, and method steps described in connection with FIG. 2A, 2B and FIG. 3, may be implemented as electronic hardware, computer software, or combinations of both, e.g. to implement the functionality described with reference to control unit 340. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the disclosure. The methods, sequences or algorithms described in connection with the control of laser devices disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of non-transitory storage medium known in the art. An exemplary storage medium is coupled to the processor such that the processor can read information from, and write information to, the storage medium. In the alternative, the storage medium may be integral to the processor.

Specific embodiments of the invention have been shown and described in detail with reference to specific examples to illustrate aspects of the invention. However, it will be understood that various modifications and changes may be made thereto without departing from the broader scope of the disclosure as set forth in the appended claims.

The invention claimed is:

1. A method for treating melasma and/or related hyperpigmentation disorders of a patient, comprising delivering laser pulses onto a body of the patient, wherein the delivering laser pulses includes the following steps:
    delivering laser pulses $p_1$ onto the body, wherein each pulse of the laser pulses $p_1$ has a diameter of at least 100 μm and a duration of at most 1 μs;
    delivering laser pulses $p_2$ onto the body, wherein each pulse of the laser pulses $p_2$ has a diameter of at least 100 μm and a duration of more than 1 μs; and
    delivering laser pulses $p_3$ onto the body, wherein each pulse of the laser pulses $p_3$ includes a plurality of microbeams each microbeam providing its own spatial local energy maximum, each microbeam having a diameter below 1 mm;
    wherein a wavelength of the laser pulses $p_1$ and a wavelength of the laser pulses $p_2$ are equal; and
    wherein a wavelength of the laser pulses $p_3$ ranges from 2 μm to 11 μm.

2. The method according to claim 1, wherein each pulse of the pulses $p_1$ has a fluence from 0.1 J/cm$^2$ to 50 J/cm$^2$ and a duration of at least 1 ps.

3. The method according to claim 1, wherein each pulse of the pulses $p_2$ has a fluence from 1 J/cm$^2$ to 100 J/cm$^2$ and a duration of at most 10 ms.

4. The method according to claim 1, wherein each pulse of the pulses $p_3$ has a fluence from 1 J/cm² to 100 J/cm² and a duration of from 0.1 ns to 100 ns.

5. The method according to claim 1, wherein each pulse of the pulses $p_1$ and/or each pulse of the pulses $p_2$ has a diameter from 1 mm to 20 mm.

6. The method according to claim 1, wherein each microbeam of the plurality of microbeams has a diameter of at least 10 μm.

7. The method of claim 1, comprising the further step of delivering laser pulse $p_4$ onto the body, wherein each pulse of the laser pulses $p_4$ has a diameter of at least 100 μm and a duration of at least 0.1 ms.

8. The method of claim 7, wherein each pulse of the pulses $p_4$ has a fluence from 10 J/cm² to 400 J/cm² and a duration of at most 100 ms.

9. The method of claim 7, comprising the further step of generating the pulses $p_4$ by a Nd:YAG laser source.

10. The method of claim 1, further comprising the step of selecting a wavelength of the laser pulses $p_1$ as a function of a depth of the melasma and/or the related hyperpigmentation disorders within a skin of the patient.

11. The method of claim 1, comprising the further step of applying a topical and/or systemic antioxidant treatment to the patient.

12. The method of claim 1, comprising the further step of generating the pulses $p_1$, $p_2$, with different laser sources.

13. The method of claim 1, comprising the further step of generating the pulses $p_1$, $p_2$, and/or $p_3$ by a Nd:YAG laser source.

14. The method of claim 1, comprising the further steps of generating the pulses $p_1$ and/or $p_2$ by a Nd:YAG laser source and/or generating the pulses $p_3$ by an Er:YAG laser source.

15. An apparatus for treating melasma and/or related hyperpigmentation disorders, comprising:
   a laser device having at least one laser source for generating laser pulses;
   at least one controller for controlling the laser device;
   wherein the controller is configured to cause the laser device to perform the following steps:
      deliver laser pulses $p_1$, wherein each pulse of the pulses $p_1$ has a diameter of at least 100 μm and a duration of at most 1 μs;
      deliver laser pulses $p_2$, wherein each pulse of the pulses $p_2$ has a diameter of at least 100 μm and a duration of more than 1 μs; and
      deliver laser pulses $p_3$, wherein each pulse of the pulses $p_3$ includes a plurality of microbeams, each microbeam providing its own spatial local energy maximum, each microbeam having a diameter below 1 mm;
   wherein a wavelength of the laser pulses $p_1$ and a wavelength of the laser pulses $p_2$ are equal; and
   wherein a wavelength of the laser pulses $p_3$ ranges from 2 μm to 11 μm.

16. The apparatus according to claim 15, wherein the at least one laser source comprises only a single laser source.

17. The apparatus according to claim 15, wherein the at least one controller comprises only a single controller and only a single laser device, and wherein the single controller is integrated, together with the at least one laser source, into the single laser device.

18. The apparatus according to claim 15, wherein the laser device comprises an applicator configured to receive laser pulses generated by the at least one laser source and to deliver them onto a patient.

19. The apparatus according to claim 18, wherein the applicator comprises a pulse geometry shaper suitable for shaping the geometry of the laser pulses directed onto the patient.

20. A computer program product, comprising:
   a computer-readable non-transitory medium comprising code for causing at least one laser device for delivering laser pulses to perform the following steps:
      deliver laser pulses $p_1$, wherein each pulse of the laser pulses $p_1$ has a diameter of at least 100 μm and a duration of at most 1 μs;
      deliver laser pulses $p_2$, wherein each pulse of the laser pulses $p_2$ has a diameter of at least 100 μm and a duration of at least 1 μs; and
      deliver laser pulses $p_3$, wherein each pulse of the laser pulses $p_3$ includes a plurality of microbeams, each microbeam providing its own spatial local energy maximum, each microbeam having a diameter below 1 mm;
   wherein a wavelength of the laser pulses $p_1$ and a wavelength of the laser pulses $p_2$ are equal; and
   wherein a wavelength of the laser pulses $p_3$ ranges from 2 μm to 11 μm.

* * * * *